United States Patent [19]

Stein et al.

[11] Patent Number: 5,342,197
[45] Date of Patent: Aug. 30, 1994

[54] DENTAL MATRIX RETAINER CLAMP

[75] Inventors: Volker W. Stein, Aurora; Robert G. Dickie, Newmarket, both of Canada

[73] Assignee: Innovadent Technologies Ltd., Newmarket, Canada

[21] Appl. No.: 182,822

[22] Filed: Jan. 19, 1994

[51] Int. Cl.$^5$ .............................................. A61C 5/04
[52] U.S. Cl. ..................................... 433/155; 433/39
[58] Field of Search .................. 433/39, 40, 155, 156, 433/157

[56] References Cited

U.S. PATENT DOCUMENTS

| | | | |
|---|---|---|---|
| 2,686,970 | 8/1954 | Reiter | 433/155 |
| 2,687,573 | 8/1954 | Stone | 433/155 |
| 2,709,302 | 5/1955 | Reiter | 433/155 |
| 3,425,125 | 2/1969 | Bergendal | 433/155 |
| 3,908,273 | 9/1975 | Reiter | 433/155 |
| 4,915,627 | 4/1990 | Hirdes | 433/155 |
| 5,055,045 | 10/1991 | Dickie et al. | 433/155 |

*Primary Examiner*—Paul J. Hirsch
*Assistant Examiner*—Nicholas D. Lucchesi
*Attorney, Agent, or Firm*—Donald E. Hewson

[57] ABSTRACT

A disposable dental matrix retainer clamp for holding a matrix band, is disclosed. The retainer clamp comprises a main body element having a generally centrally located first longitudinal axis and first and second opposed lateral sides. A head element having a first end, a second end, a generally centrally located second longitudinal axis extending from the first end to the second end, an anterior surface having a guide slot centrally located therein through which the matrix band extends, and a pivot axis perpendicular to the first longitudinal axis is pivotally mounted on the main body element by way of a pair of oppositely directed mounting posts received in co-operating apertures that are located one each in respective opposed flange members extending outwardly from the main body element between a first locked position, a second locked position, and an intermediate position therebetween. First and second locking means in the form of detent portions on the main body element interact in an interference relation with cooperating protruding portions on the first and second ends of the head element, the first and second locking means thereby being adapted to lock the head element in a first or second locked position respectively. The mounting posts are each engaged in loosely held relation in the co-operating apertures so as to allow lateral movement of the mounting posts with respect to the main body element, to thereby accommodate the interference fit between the first and second ends and the respective of the first and second detent portions.

13 Claims, 2 Drawing Sheets

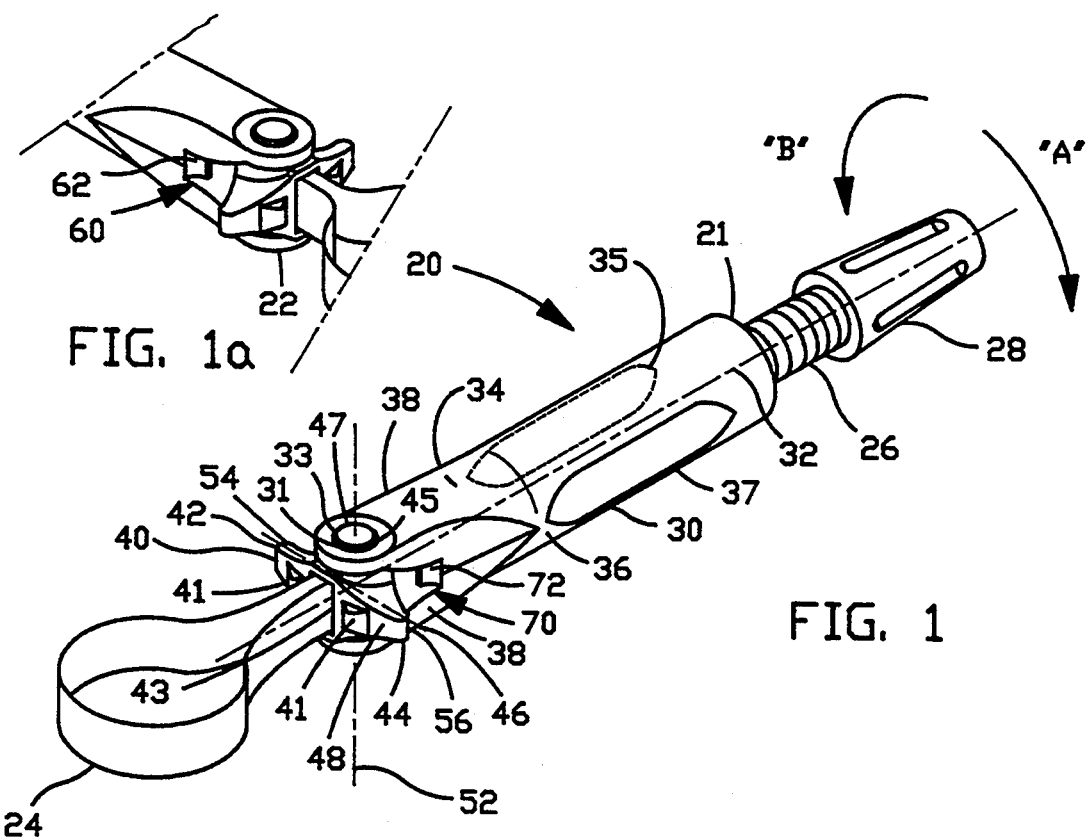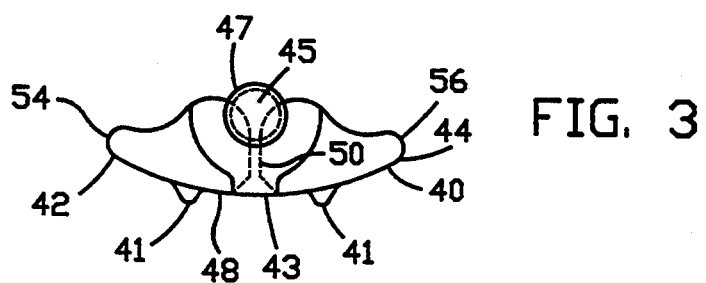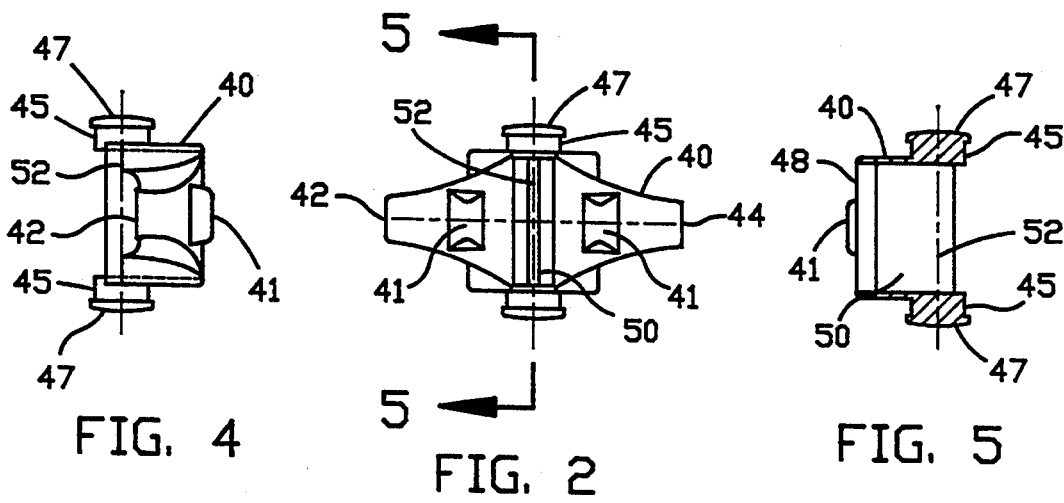

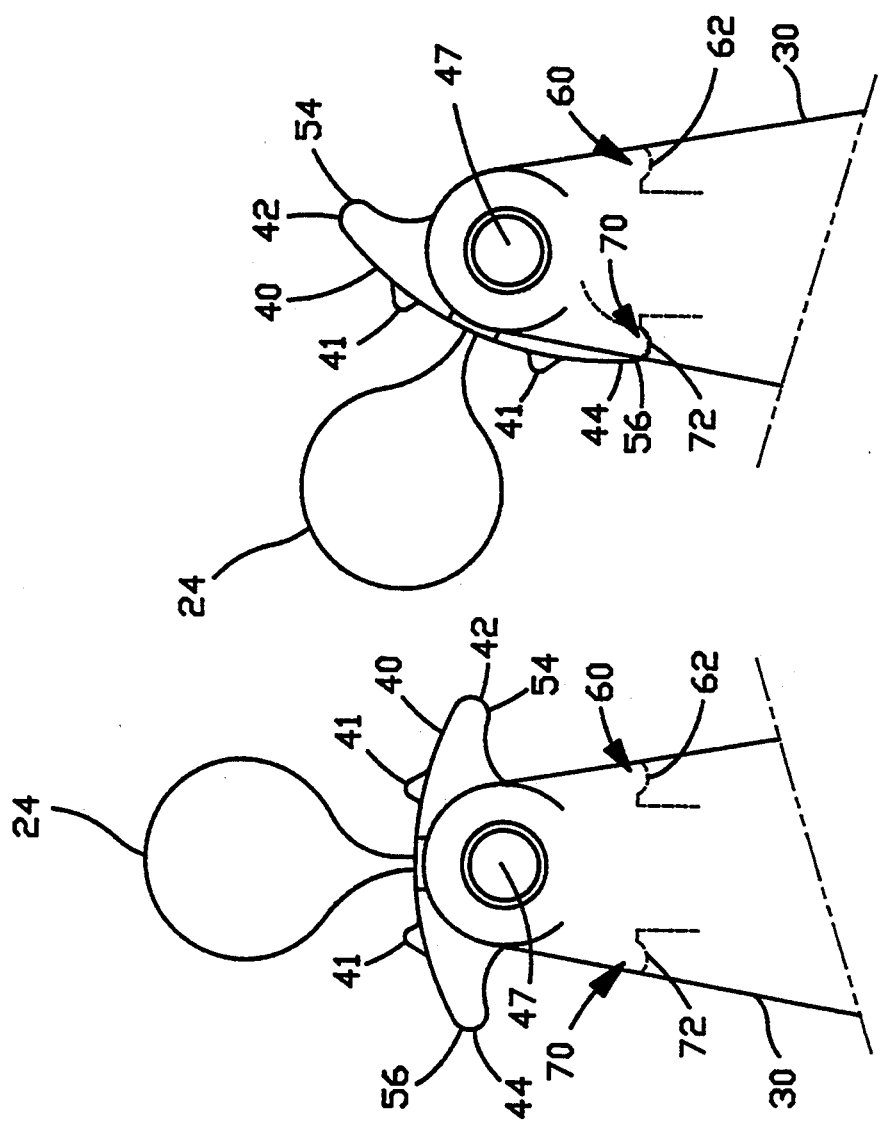
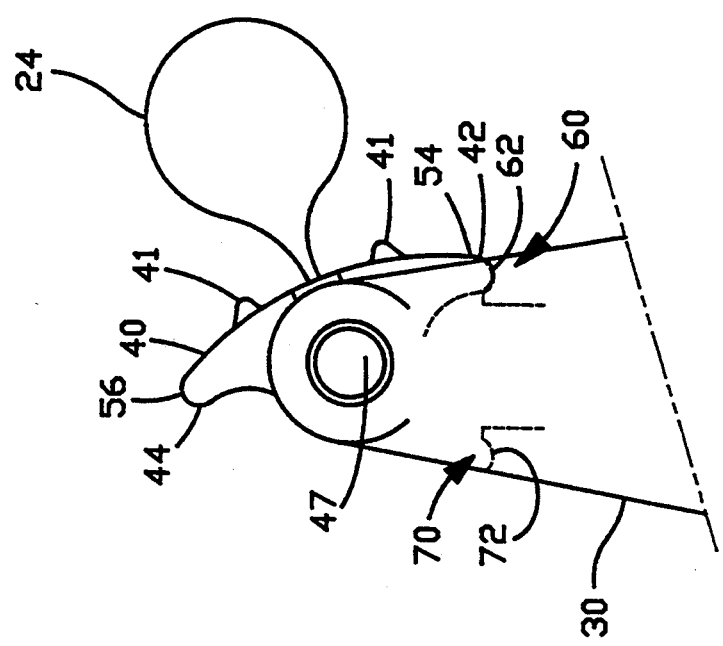
FIG. 8
FIG. 7
FIG. 6

DENTAL MATRIX RETAINER CLAMP

FIELD OF THE INVENTION

This invention relates to devices used in dentistry and more particularly to dental implements adapted for temporary firing within a patient's mouth. Specifically, an improvement in dental matrix retainer claps is disclosed.

BACKGROUND OF THE INVENTION:

Dental matrix retainer claps are used by dentists to permit missing portions of a tooth to be replaced following cavity preparation, so that an amalgam, composite resin, or temporary dressing may be inserted. State of the art dental matrix retainer clamps typically comprise a main body element and a head element pivotally mounted on the main body element. A narrow band of very thin metal is operatively retained by a the retainer clamp so as to exit one end of the head element through a co-operating centrally located slot in the head element. The metal matrix band tends to bias the head element towards a generally medial angular orientation with respect to the holding element due to the springiness of the metal material. The ends of the metal matrix band are retained within the main body element and the remainder of the metal matrix band forms a loop exterior to the retainer clamp. In use, the loop is fitted around a tooth and an adjustment mechanism integral with the main body element allows for adjustment of the size of the loop.

The head element is typically angularly adjustable with respect to the main body element so as to permit the main body element to be positioned away from the tooth being worked on and positioned towards the adjacent teeth. When the metal matrix band is in place around a tooth, retained securely thereat by a dental matrix retainer clamp, it is desirable that the head element be retained as far as possible to one side or the other, at an extreme angular position, in order to keep the holding element from getting in the way of the dentist as he accesses the tooth being worked on. Due to the springiness of the metal matrix band that passes through the head element, it is difficult to keep the head element retained as far as possible to one extreme side or the other of the holding element. Means to properly and adequately retain the head element of a dental matrix retainer clamp in a given position, especially an extreme position, with respect to its holding mechanism, are not known in the prior art.

U.S. Pat. No. 5,055,045, which issued to the present inventors, discloses a dental matrix retainer clamp that has an angularly adjustable head element. The angular position of the head element is maintained by way of a mounting pin on the main body element that frictionally engages the head element. It has been found that this above described arrangement does not provide adequate retention of a set position of the head element with respect to the main body element, as the main body element may be easily moved slightly with respect to the head element. Especially, it does not provide for adequate retention of a set position if the head element is at an extreme angular position, as the metal matrix band tends to bias the head element back towards a central position.

German Patent 26 03 130, published Aug. 4, 1977, discloses a dental matrix retainer clamp wherein there is a hollow tube and a head element that contains a slot that is mounted at the end of the tube. An adjusting knob is provided, and the head element can be rotated so that a band protruding from the head element can be oriented at an angle to the longitudinal axis of the body. Moreover, the present invention is specifically directed to a dental matrix retainer clamp which can be used only once and which must be discarded after use.

It is an object of the present invention to provide a head element for use in conjunction with a dental matrix retainer clamp, wherein the head element is securely retained in at least one set angular position with respect to the holding mechanism of the dental matrix retainer clamp.

It is another object of the present invention to provide a head element for use in conjunction with a dental matrix retainer clamp, wherein the head element is securely retained in an extreme set angular position with respect to the holding mechanism of the dental matrix retainer clamp.

A further problem is encountered with prior art dental matrix retainer clamps when the metal matrix band is tightened in place on a tooth. The head element is not securely positioned in supporting relation against the metal matrix band that is looped around a tooth, even when the head element is at an extreme angular position. The head element does not therefore help support the metal matrix band against the tooth. It is important, or at least desirable, that the head element remain in supporting relation against the metal matrix band looped around a tooth. An adequate and proper anterior surface for the head element, especially one that provides adequate and proper support for the metal matrix band, is not known in the prior art.

It is an object of the present invention to provide a head element that has an adequate and proper anterior surface adapted to securely support the metal matrix band of the dental matrix retainer clamp in substantially unmoving supportive engagement with a tooth.

SUMMARY OF THE INVENTION

In one aspect of the present invention there is provided a disposable dental matrix retainer clamp for holding a metal matrix band in secure relation on a person's tooth. The retainer clamp comprises a main body element having a generally centrally located first longitudinal axis and first and second opposed lateral sides. The head element has a first end, a second end, an anterior surface having a guide slot centrally located therein through which the matrix band extends, and a pivot axis perpendicular to the first longitudinal axis. The pivot axis is located midway between the first and second opposed lateral sides of the main body element. The head element has a generally centrally located second longitudinal axis extending from the first end to the second end. The head element is movably mounted on the main body element by way of a mounting means for angularly variable movement about the pivot axis, the angular variably movement being with respect to the main body element between a first locked position, a second locked position, and an intermediate position therebetween. A first locking means in the form of a first detent portion on the main body element interacts with a co-operating protruding portion on the head element. The first locking means is thereby adapted to lock the head element in the first locked position, whereat the first end of the head element is disposed toward the first lateral side of the main body element.

Similarly, a second locking means in the form of a second detent portion on the main body element interacts with a co-operating protruding portion on the head element. The second locking means is thereby adapted to lock the head element in the second locked position, whereat the second end of the head element is disposed toward the second lateral side of the main body element.

In order to retain the looped metal matrix band relatively securely against a tooth with no more than the minor mount of relative movement, the head element has a pair of opposed supporting shoulders that are suitable for supportive engagement with the portion of the metal matrix band that is juxtaposed the labial surface of a tooth.

DESCRIPTION OF THE DRAWINGS

Embodiments of the present invention will now be described by way of the accompanying drawings, in which:

FIG. 1 is a perspective view of the dental matrix retainer clamp of the present invention;

FIG. 1a is a partial perspective view of the opposite side of the end of the dental matrix retainer clamp of the present invention;

FIG. 2 is a front end view of the head element of the dental matrix retainer clamp of FIG. 1;

FIG. 3 is a top view of the head element of FIG. 2;

FIG. 4 is an end view of the head element of FIG. 2;

FIG. 5 is a cross-sectional view of the head element of FIG. 2, taken along section line 5—5;

FIG. 6 is a top plan view of the dental matrix retainer clamp with the head element in a first locked position;

FIG. 7 is a top plan view of the dental matrix retainer clamp with the head element in an intermediate position; and FIG. 8 is a top plan view of the dental matrix retainer clamp with the head element is a second locked position.

DETAILED DESCRIPTION OF THE PREFERRED EMBODIMENTS

Reference will now be made to FIG. 1, which shows the disposable dental matrix retainer clamp 20 of the present invention with a metal matrix band 24 retained therein. The matrix retainer clamp 20 has a main body element 30 with a head element 40 operatively mount thereon. The main body element 30 has a generally centrally located first longitudinal axis 32, and first and second opposed lateral sides 34 and 36. The first and second opposed lateral sides 34, 36 preferably each have a flat portion 35, 37 thereon, which flat portions 35, 37 are adapted to receive a person's thumb and one finger in grasping relation thereon. A pair of opposed flange members 38 extend outwardly from the main body portion 30 in spaced apart generally parallel relation one to the other, and are thereby adapted to receive and retain the head element 40 in operative relation therebetween, as will be discussed in greater detail subsequently.

The matrix metal band 24 is in the form of a loop extending outwardly from the head element 40 through a generally centrally located guide slot 50. The two ends of the metal matrix band 24 are operatively retained within the main body element 30 on an adjustment mechanism in the form of a threaded rod 26, so as to thereby make the loop size of the metal matrix band 24 adjustable. The threaded rod 26 is threadibly engaged by the main body element 30, and extends outwardly from the back end 21 thereof. A gripping member 28 is formed on the end of the threaded rod 26 so as to permit the threaded rod 26 to be readily turned with respect to the main body member 30. When the gripping member 28 is turned in a first direction, as indicated by arrow "A", an internal release mechanism (not shown) is engaged and the metal matrix band 24 is extended so as to increase the size of the loop that it forms. When the gripping member 28 is rotated in an opposed second direction, as indicated by arrow "B", the metal matrix band 24 is retracted, thereby decreasing the loop size, so as to tighten the matrix band 24 securely around a tooth. The internal mechanism that receives and retains the metal matrix band 24 and permits the tightening and relaxing thereof is taught in U.S. Pat. 5,055,045.

The head element 40 has a first end 42, a second end 44 and a generally centrally located second longitudinal axis 46 that extends from the first end 42 to the second end 44. The head element 40 is divided into two symmetrical halves at the second longitudinal axis 46, and is thereby longitudinally symmetrical. An anterior surface 48 is adapted to interface with the outer facing portion of a tooth by way of a pair of opposed supporting shoulders 41, one supporting shoulder on each of the symmetrical halves of the head element 40. Between the pair of the opposed supporting shoulders 41 is a recessed area 43 that has the guide slot 50 centrally located therein. The head element 40 is pivotally mounted on the front end 22 of the matrix retainer clamp for angularly variable movement about a pivot axis 52 that is perpendicular to the first longitudinal axis and located midway between the first and second opposed lateral sides, 34, 36.

The supporting shoulders 41 on the anterior surface 48 are shaped and dimensioned to be in supporting contact with the metal matrix band 24, when the matrix band 24 is snugly in place around a tooth, on an as needed basis, depending on the shape and size of the tooth being worked on. The supporting shoulders 41 preclude the loop of the metal matrix band 24 that is in place around a tooth from moving laterally with respect to the head element 40, thereby allowing the matrix band 24 to be kept in proper placement around the tooth.

Preferably, the mounting means is in the form of a pair of oppositely directed mounting posts 45 that are received in co-operating apertures 31 located one each on respective of the opposed flange members 38. In this manner, the head element 40 is pivotally mounted with respect to the main body element 30 between a first locked position, as shown in FIG. 6, whereat the head element 40 is disposed toward the first lateral side 34 of the main body element 30 and a second locked position, as shown in FIG. 7, whereat the second end 44 of the head element is disposed toward the second lateral side 36 of the main body element 30. The first and second locked positions correspond to the "in-use" positions of the dental matrix retainer clamp 20 in a person's mouth, whereat the main body element 30 is disposed to one side of the tooth being worked on. There is also an intermediate position therebetween, which intermediate position substantially bisects the first and second locked positions such that the second longitudinal axis 46 passes through it. Thus, at rest, the orientation of the second longitudinal axis 46 is substantially perpendicular to the first longitudinal axis 32.

In order to lock the head element 40 in its first locked position, there is a first locking means 60 in the form of a first detent portion 62 on the main body element 30. The first detent portion 62 interacts with a co-operating first protruding portion 54 at the first end 42 of the head element 40. Similarly, in order to lock the head element 40 in its second locked position, a second locking means 70 in the form of a second detent portion on the main body element interacts with a co-operating second protruding portion 56 at the second end 44 of the head element 40. The first detent portion 62 retains the first end 42 of the head element 40 in an interference fit therewith when the head member 40 is in its first locked position. Similarly, the second detent portion 72 retains the second end 44 of the head element 40 in an interference fit therewith when the head member is its second locked position. In order for this interference fit type of locking mechanism to work properly the head element 40 will deform slightly in order to permit the first and second protruding portions 54, 56 to move past the respective of the first and second detent portions 62, 72.

It should be noted that the dental matrix retainer clamp 24 is symmetrical from side to side about the first longitudinal axis 32 and is symmetrical from top to bottom about the first longitudinal axis 32. Accordingly, locking the head element 40 in its first locked position is completely equivalent to locking the head element 40 in its second locked position. The advantage of being able to lock the head element 40 in either are one of the first and second positions is that the dental matrix retainer clamp can be used on teeth on either side of a patient's mouth in an equivalent manner. Keeping in mind that the loop formed by the metal matrix band 24 is lightly tapered—that is to say that it is slightly larger at its first edge 24a and slightly smaller at its second edge 24b—it must be engaged on a tooth with the first edge 24a against the gingiva and the second edge 24b at the top of the tooth. Accordingly, the head element 40 is in its first locked position when in place on a patient's tooth in the upper right or lower left quadrant of the mouth, and is in its second locked position when in place on a patient's tooth in the upper left quadrant or the lower right quadrant of the mouth.

In order to properly accommodate the interference fit type locking mechanism of the first locking means 60 and second locking means 70, the head element 40 is somewhat loosely retained by the main body element 30. More particularly, the mounting posts 45 are engaged in loosely held relation in the co-operating apertures 31 so as to allow a small amount of lateral movement of the mounting posts 45 with respect to the main body element 30. Such lateral movement of the mounting posts 45 allows the interference fit between the first and second ends of the head element 40 and the respective of the first and second detent portions 62, 72 to be accommodated. This means that, in practice, the diameter of each of the mounting posts 45 is approximately 0.15 mm less than the diameter of the co-operating apertures 31. This 0.15 mm difference in dimensions provides for a slightly larger clearance than a difference of about 0.05 mm, which would normally be the difference in dimensions that is typically found in a conventional interference fit configuration of two small plastic pieces. If a conventional clearance of about 0.05 mm were to be provided between the mounting posts 45 and the co-operating apertures 36, the passing of the first and second protruding portions 54, 56 over the respective first and second detent portions 62, 72 would be accommodated mostly by the deformation of the head element 40 and accommodated to a small degree by the 0.05 mm clearance. In that event, an undue force must be applied to the head element in order to move the head element 40 into or out of either of its first or second locked positions. However, because of the small size of the head element 40, the moment arm between the ends 42, 44 of the head element 40 and its pivot point are each quite small. Thus, a somewhat large force—usually applied at one of the ends 42,44—would be required to manipulate the head element into or out of the first and second locked positions. Therefore, it would be difficult to snap the head element 40 into its first and second locked positions if a clearance of about 0.05 mm were used in conjunction with a conventional interference-fit type locking means.

In the present invention, therefore, in order for the locking and the unlocking of the head element to be relatively easily performed, it is necessary that only a relatively small operating force by the fingers be required. To functionally minimize such forces, the interference fit between either of the first and second ends 42, 44 of the head element 40 and the respective of the first and second detent portions 62, 72 must be functionally minimized. At the same time, the first and second ends 42, 44 must be sufficiently blocked by the respective of the first and second detent portions 62, 72 so as to hold the head element in the respective of its first and second locked configurations. These seemingly contradictory requirements are indeed met by the slightly larger-than-conventional clearance between the mounting posts 45 and the co-operating apertures 36 of 0.15 mm. This particular clearance allows the head element to move laterally during locking and unlocking, so that the physical displacement of the material of the head element 40 that is required to allow the ends 42, 44 to move past the respective first and second detent portions 62, 72 is reduced to an optimum level.

It is therefore desirable to use a slightly larger-than-conventional clearance between the mounting posts 45 and the co-operating aperture 36 so that the deformation of the head element 40 is reduced during locking and unlocking of the head element 40. In this manner, manipulation of the head element 40 into and out of either of the first and second locking positions is possible, by way of relatively low force thumb and finger operation.

The mounting posts 45 each have an enlarged head portion 47 thereon and the co-operating apertures 36 have an enlarged end portion 33, with the enlarged end portions 33 each adapted to receive the respect of the large head portion 47 therein, so as the thereby securely retain the head element 40 within the flange members 38. The diameter of each of the enlarged head portions 47 of the mounting posts 45 is at least 0.15 mm less than the cooperating enlarged end portions 33 of the apertures 31, but is also about 0.15 mm larger than the diameter of the co-operating apertures 36. This slightly larger dimension of the enlarged end portions 33 permits the head element 40 to be relatively securely retained between the flange members 38.

When the disposable dental matrix retainer clamp is to be used, a decision is first made to move the main body element 30 out of the way of the tooth, at least as much as possible so that the tooth may be worked on. Thus, the main body element 30 is pivoted to one side or the other and may then be locked in place in either of the first or second locked positions, as appropriate, so as to remain out of the way. Then, an adjustment is made so that the size of the loop formed by the metal matrix band 24 is at least large enough to fit over the tooth. The metal matrix band 24 is then placed in the mouth around the tooth, and the gripping member 28 is turned in the second direction, as indicated by arrow "B", so as to pull the end of the metal matrix band 24 into the main body element 30 and to thereby tighten the metal matrix band onto the receiving tooth. The dental procedure then continues.

Other modifications and alterations may be used in the design and manufacture of the dental matrix retainer clamp of the present invention without departing form the spirit and scope of the accompanying claims.

What is claimed is:

1. A disposable dental matrix retainer clamp for holding a matrix band, said retainer clamp comprising:
   a main body element having a generally centrally located first longitudinal axis and first and second opposed lateral sides;
   a head element having a first end, a second end, a generally centrally located second longitudinal axis extending from said first end to said second end, an anterior surface having a guide slot centrally located therein through which the matrix band is adapted to extend, and a pivot axis perpendicular to said first longitudinal axis and located mid-way between said first and second opposed lateral sides;
   wherein said head element is movably mounted on said main body element by way of a mounting means for angularly variable movement about said pivot axis and with respect to said main body element between a first locked position, a second locked position, and an intermediate position therebetween;
   a first detent portion on one of said head element and said main body element and a first protruding portion on the other of said head element and said main body element, said first detent portion and said first protruding portion adapted for co-operating interference fit with one another so as to thereby form a first locking means that is adapted to lock said head element in said first locked position when said first end of said head element is disposed toward said first lateral side of said main body element; and
   a second detent portion on one of said head element and said main body element and a second protruding portion on the other of said head element and said main body element, said second detent portion and said second protruding portion adapted for co-operating interference fit with one another so as to thereby form a second locking means that is adapted to lock said head element in said second locked position when said second end of said head element is disposed toward said second lateral side of said main body element.

2. The disposable dental matrix retainer clamp of claim 1, wherein said first detent portion and said second detent portion are on said main body element, and said first protruding portion and said second protruding portion are on said head element.

3. The disposable dental matrix retainer clamp of claim 2, wherein said first detent portion interacts with said first end of said head element and said second detent portion interacts with said first end of said head element.

4. The disposable dental matrix retainer clamp of claim 3, wherein said head element is pivotally mounted on said main body element by way of a pair of oppositely directed mounting posts received in co-operating apertures in said main body element.

5. The disposable dental matrix retainer clamp of claim 4, wherein each of said mounting posts is engaged in loosely held relation in a respective one of said co-operating apertures so as to allow lateral movement of said mounting posts with respect to said main body element, to thereby accommodate the interference fit between said first and second ends and the respective of said first and second detent portions.

6. The disposable dental matrix retainer clamp of claim 5, further comprising a pair of opposed flange members projecting outwardly from said main body element.

7. The disposable dental matrix retainer clamp of claim 6, wherein said co-operating apertures are in said opposed flange members, one aperture in each flange member, said flange members thereby adapted to receive and retain said head element in operative relation therewith.

8. The disposable dental matrix retainer clamp of claim 4, wherein the diameter of each of said mounting posts is approximately 0.15 mm less than the diameter of each of said co-operating apertures.

9. The disposable dental matrix retainer clamp of claim 4, wherein each of said mounting posts has an enlarged head portion thereon and each of said apertures has a co-operating enlarged end portion adapted to receive the respective one of said enlarged head portions therein, so as to thereby securely retain said head element within said flange members.

10. The disposable dental matrix retainer clamp of claim 1, wherein said intermediate position substantially bisects said first and second locked positions such that said second longitudinal axis passes through an orientation that is substantially perpendicular to said first longitudinal axis.

11. The disposable dental matrix retainer clamp of claim 10, wherein said head element is longitudinally symmetrical so as to define two symmetrical halves.

12. The disposable dental matrix retainer clamp of claim 11, wherein said anterior surface of said head element comprises a pair of opposed supporting shoulders, one supporting shoulder located on each of said symmetrical halves.

13. The disposable dental matrix retainer clamp of claim 12, further comprising a recessed area between said pair of opposed supporting shoulders.

* * * * *